(12) United States Patent
Sobol et al.

(10) Patent No.: US 11,835,507 B2
(45) Date of Patent: Dec. 5, 2023

(54) SYSTEMS, SUBSYSTEMS AND METHODS FOR MEASURING WATER CHARACTERISTICS IN A WATER FACILITY (71) Applicant: Maytronics Ltd., Kibbutz Yizrael (IL)

(72) Inventors: Shahar Sobol, Haifa (IL); Alexander Rachman, Katzir (IL); Hanoch Kislev, Zichron Yaakov (IL); Igor Lulko, Hertzliya (IL)

(73) Assignee: Maytronics Ltd., Kibbutz Yizrael (IL)

(*) Notice: Subject to any disclaimer, the term of this patent is extended or adjusted under 35 U.S.C. 154(b) by 0 days.

(21) Appl. No.: 17/677,653

(22) Filed: Feb. 22, 2022

(65) Prior Publication Data
US 2022/0268753 A1 Aug. 25, 2022

(51) Int. Cl.
G01N 33/18 (2006.01)
H04R 1/08 (2006.01)
G01N 29/02 (2006.01)
G01N 21/31 (2006.01)

(52) U.S. Cl.
CPC ............ G01N 33/18 (2013.01); G01N 21/31 (2013.01); G01N 29/02 (2013.01); G01N 33/1826 (2013.01); G01N 33/1853 (2013.01); H04R 1/08 (2013.01); G01N 2291/0228 (2013.01)

(58) Field of Classification Search
None
See application file for complete search history.

(56) References Cited

U.S. PATENT DOCUMENTS

| 6,002,990 A | 12/1999 | Hanna |
| 10,151,633 B2 * | 12/2018 | O'Rourke ............ G01N 21/3103 |
| 10,302,564 B2 | 5/2019 | Hasegawa et al. |
| 2018/0224334 A1 | 8/2018 | O'Rourke et al. |
| 2018/0266131 A1 * | 9/2018 | Witelson ............ G01N 33/1826 |

FOREIGN PATENT DOCUMENTS

| EP | 3213055 A1 * | 9/2017 | ............ G01N 21/31 |
| EP | 3719495 A1 | 10/2020 | |
| WO | 2020/031183 A1 | 2/2020 | |

* cited by examiner

Primary Examiner — Daniel S Larkin (57) ABSTRACT

Systems and Methods for monitoring characteristics of a water sample taken from a water facility (WF), by using a first light source emitting light at a first wavelength, and an additional light source, emitting light at an additional wavelength which is distinctly different from the first wavelength; for each light source, performing a measurement of the water sample, using an optical sensor outputting updated sensor data and a spectral detector, outputting updated detector data; and determining adjustment properties for adjustment of an analysis model, used for ongoing determination of water characteristics such as the water turbidity level, based on comparison between the measurements for each of the light sources.

20 Claims, 7 Drawing Sheets

SYSTEMS, SUBSYSTEMS AND METHODS FOR MEASURING WATER CHARACTERISTICS IN A WATER FACILITY

The present disclosure relates in general to systems and methods for measuring water-quality related characteristics for water of a water facility.

BACKGROUND

The level or rate of turbidity of a liquid may be referred to as the level of "optical density" of the liquid.

There may be many factors that influence water turbidity level such as chemical pollutants' crystallization, biomass growth (e.g., algae/microalgae growth), erosion-originated sediments, airborne pollutants reaching the water facility, etc. These chemical and/or biological pollutants in swimming-pool water, pose constant threat to public health and require stubborn and consistent counter-acting monitoring and treatment.

BRIEF DESCRIPTION OF THE FIGURES

The figures illustrate generally, by way of example, but not by way of limitation, various embodiments discussed in the present document.

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. References to previously presented elements are implied without necessarily further citing the drawing or description in which they appear. The figures are listed below.

According to some embodiments, at least some of the functions and operations of the system may be carried out and controlled in a completely automatic manner, such as, for example, the ongoing water-quality (turbidity level and pollutants concentration) measuring/monitoring, the system impairments inspection, etc.

FIGS. 1A and 1B schematically illustrate a system for measuring water-quality related characteristics of water sampled from a water facility, using two light sources for detection of system impairments, according to some embodiments: FIG. 1A shows a side view of the system; and FIG. 1B shows a side cross-sectional view of the system;

FIG. 4A shows a flowchart, schematically illustrating a process for adjusting an analysis model, the analysis model used for determining water characteristics, according to some embodiments;

DETAILED DESCRIPTION OF EMBODIMENTS

Aspects of disclosed embodiments pertain to systems and methods for automatic and ongoing measuring of one or more water-quality related characteristics of liquid such as water in a water facility, such as, for measuring turbidity level and/or concentration/quantity of biological and/or chemical particles in the water such as concentration/quantity of algae, microalgae or chemical particles (pollutants) that increase water turbidity. The water characteristics measurements may be done as an ongoing continuous or frequent process for enabling ongoing water quality and/or water facility monitoring.

According to some embodiments, the water-quality monitoring may be based mainly, yet not exclusively, on measuring optical characteristics of the water, using at least one spectral detector, such as a spectrometer and an optical setup designed for directing light towards a sampled portion of the water to be tested/monitored, where the spectrometer, may be used for measuring light that is passed through the sampled water, where opacifying polluting particles/biomass, such as algae, may cause the sampled water to irradiate and/or scatter light of distinctive detectable optical characteristics (e.g. by causing water fluorescence). This may enable optically measuring (or calculating based on optical measuring) the water turbidity level and/or optionally also other water-quality related characteristics such as pollutants' type (chemical/biological, specific biological mass type and/or specific chemical compounds, etc.), pollutants' concentration or quantity and the like.

According to some embodiments, the general turbidity level of the sampled water may be done using spectrometric analysis of scattered light in the water sample, whereas an algae concentration/quantity value may be acquired based on identification and analysis of fluorescence response of the algae cells (or any other biomass) to the incoming light irradiating the water sample, e.g. originating from a light source of a distinctive narrow wavelength (WL) peak, for example in the near-blue WL range (e.g. between 300-450 nanometers (nm)).

In some embodiments, one or more additional optical sensors can be used such as a RGB (red green blue) sensor, a charged couple device (CCD) or a photodiode sensors, for improving turbidity level and/or algae concentration/quantity detection by comparing overall power/intensity of the light source, sensed by the additional sensor, to the spectral detector output, for improving, for example, identification of algae fluorescence response to the irradiation of the water sample emanating from the light source.

According to some embodiments, the updated turbidity level of the water sample may be calculated (by the analysis model) according to the following mathematical relation between the overall power of the light source irradiating the water sample, and the spectrometer detected data:

$$P = P_{LED} k C_a \quad (1)$$

Where "Pt" is the power of signal acquired by the spectral detector, "$P_{LED}$" is the overall power of light of the respective light source (e.g. as sensed by the optical sensor or provided as a constant known value), "$C_a$" is the scattered particles concentration (to be calculated), and "k" is a constant which represents optical losses, coupling efficiency and large angle scattering cross section.

In other embodiments, the spectral detector probes induced algae fluorescence response to the light irradiation, e.g. emitted in red-shifted wavelengths. The fluorescence signal "$P_{alg}$" can be calculated from Eqn. 2

$$P_{alg} = P_{LED} k_f C_{alg} \sigma_f \qquad (2)$$

Where "$C_{alg}$" is the algae concentration and "$\sigma_f$" is the algae fluorescence cross-section, respectively, and "$k_f$" is a constant which represents fluorescence optical losses, coupling efficiency water illumination factor.

According to some embodiments, the system may include:
- a sampling unit comprising a sample of water from the water facility e.g. contained by a cuvette;
- at least one light source such as a first light source, configured to emit light of a distinctive WL peak (e.g., within the range of 400-450 nm e.g., 420 nm);
- an optical sensor such as a RBG sensor, a photodiode etc., configured to detect at least portion of an overall power/intensity of light directly emitted by the at least one light source (e.g. outputting a sensor output signal proportional/indicative of the overall intensity of the respective light source);
- an optical setup, comprising at least one optical element (e.g. a collimator and/or a focusing lens), configured to direct light emitted by the first light source towards the optical sensor and towards the sampling unit such that the light emitted by the at least one light source irradiates the water in the sampling unit for enabling scattering and/or fluorescence of the light, by particles (biological or chemical) in the sampled water;
- at least one spectral detector such as a spectrometer, configured and positioned such as to detect spectral characteristics of light exiting from the sampling unit (e.g., including scattered/fluorescent light); and
- a processing unit configured to receive updated sensor data from the at least one optical sensor and updated detector data from the spectral detector, perform an analysis of the received updated detector and sensor data, using an analysis model, and determine, based on the data analysis, one or more updated water-quality related characteristics of the sampled water. The updated water-quality related characteristics may include at least updated turbidity level of the sampled water and/or algae or other pollutants concentration and/or quantity.

The analysis model may be any hardware-based and/or software-based program or algorithm, enabling processing of received data and/or signals. According to some embodiments, the analysis model may be adjustable based on accumulated and/or updated analysis results. For example, the analysis model may be programmed to be automatically adjusted (e.g., by adjusting threshold values, parameters values, coefficients values in mathematical programs/algorithms used by the model) based on updated identified impairments or changes in light source(s) and/or spectrometer performances.

According to some embodiments, the system may enable calibration of the analysis model by using two different measurement sessions one using one light sources of a first output WL and another light source of a second output WL distinctively different than the first WL, for adjusting coefficients, factors, thresholds etc. of the analysis model based on comparison between spectrometer and optical detector output data for each measurement session i.e. for each of the different light sources.

According to some embodiments, the optical setup of the system may include collimating and focusing means for collimating/collecting a significant portion of light of the light source at work and directing it (e.g., in a collimated or focused manner) towards the water sample. The optical setup may also be configured to direct some other portion of the light from the light source towards the optical sensor, for direct measurement of the light source's output power or a signal indicative of the light source's output power related characteristics such as light flux, intensity, amplitude, spectral characteristics such as peak WL/frequency, etc.

According to some embodiments the system may include at least one additional light source of a distinctively different WL peak (e.g., within the range of 300-380 e.g., 365 nm), for enabling using a reference light source for calibration and/or updated adjustment of the spectral detector e.g., by comparing spectral detector output data for each separate light source for identification of spectral impairments or changes such as spectral drifts of the spectral detector or of the first light source.

The spectral characteristics such as spectral drifts indicated in or deduced from the updated detector data may be influenced in response to changes in various internal and/or external conditions such as in response to temperature value, temperature gradient, and/or other environmental or other influences and changes occurring in the area of the light sources, the area of the spectral detector, the spectral detector functionality, and/or in the water sample.

According to some embodiments, the processing model may be configured to distinguish between spectral drifts that do not require calibration or adjustment of the analysis model and cases that do require such adjustment. For instance, the processing model may be configured to identify spectral drifts caused due to substantial rise and/or drop in temperature (e.g. temperature gradient exceeding a predefined threshold) in the area of the light source(s) caused by natural heating of the light source lamp(s) (e.g. by using one or more thermometers or temperature sensors located near the light source(s)), in which case, simple deactivation (off switching) of the respective light source for a predefined cooling timeframe may be required rather than adjusting the analysis model. In cases in which the spectral drifts are identified as requiring adjustment of factors such as adjustment of coefficients and/or threshold values of the analysis model, the actual drift(s) rate(s)/value(s) may be checked and the adjustment may only be required upon a drift that exceeds a predefined WL drift threshold (e.g. a drift of over 1 or 2 nanometers).

According to some embodiments the processing unit may also be configured to operate and control operation of any one or more of: (i) the at least one optical sensor; (ii) the at least one spectral detector; (iii) each of the at least one light source.

According to some embodiments, for monitoring or inspecting the functioning of the spectral detector and/or the functioning of the first light source, using the additional light source, the processing unit may be programmed to carry out routine, frequent or required system impairments inspections sessions, for instance, by controlling switching of the light source from one to another (for separate spectral measurement sessions) and carrying out an inspection processing of the received spectral data (e.g. using an inspection model) as well as enabling adjusting the analysis model based on inspection analysis results.

According to some embodiments, the system may also use one or more acoustic transducers such as one or more piezoelectric transducers for water-treatment e.g. for preventing or reducing pollutants concentration inside the cuvette, for cleaning of the cuvette, for turbidity level measuring improvement, and/or for measuring water-hardness rate. The processing unit may be further configured to operate and coordinate operation of the acoustic transducer for conducting frequent or required "water-hardness" checks for determining water-hardness level, based on acoustic and optionally also based on optical water sample measurements, e.g. using a preset hardness check procedure. Additionally or alternatively routine cuvette cleaning sessions may be carried out by controlled operation of the acoustic transducer The term "water hardness" may relate, for example, to the concentration of specific chemical components dissolved or suspended in the water such as dissolved calcium and/or magnesium concentration.

According to some embodiments, the acoustic transducers may be configured to be operated within the ultrasonic (US) acoustic frequency range such as, for example a 10-40 kHz range.

According to some embodiments, the US frequency or frequency band used for cuvette cleaning may be different from the US frequency of frequency band used for water hardness level testing.

According to some embodiments, the water-hardness rate detection procedure may include the steps of:
- measuring a pre-US-treatment turbidity level of water sample: $T_1$;
- applying an ultrasonic treatment to the water-sample (e.g. by transmitting an US signal of a constant/changing frequency and/or modulation during a predefined time period $\Delta t$ e.g. of a few seconds or a few minutes);
- measuring updated post-US-treatment turbidity level $T_2$ of the water sample (after the applying of the US treatment);
- comparing the pre-US-treatment turbidity level $T_1$ with the post-US-treatment turbidity level $T_2$ (e.g. by calculating turbidity difference: $\Delta T=|T_2-T_1|$); and
- deducing/calculating the water-hardness rate based on the comparison results.

Figure 1A:
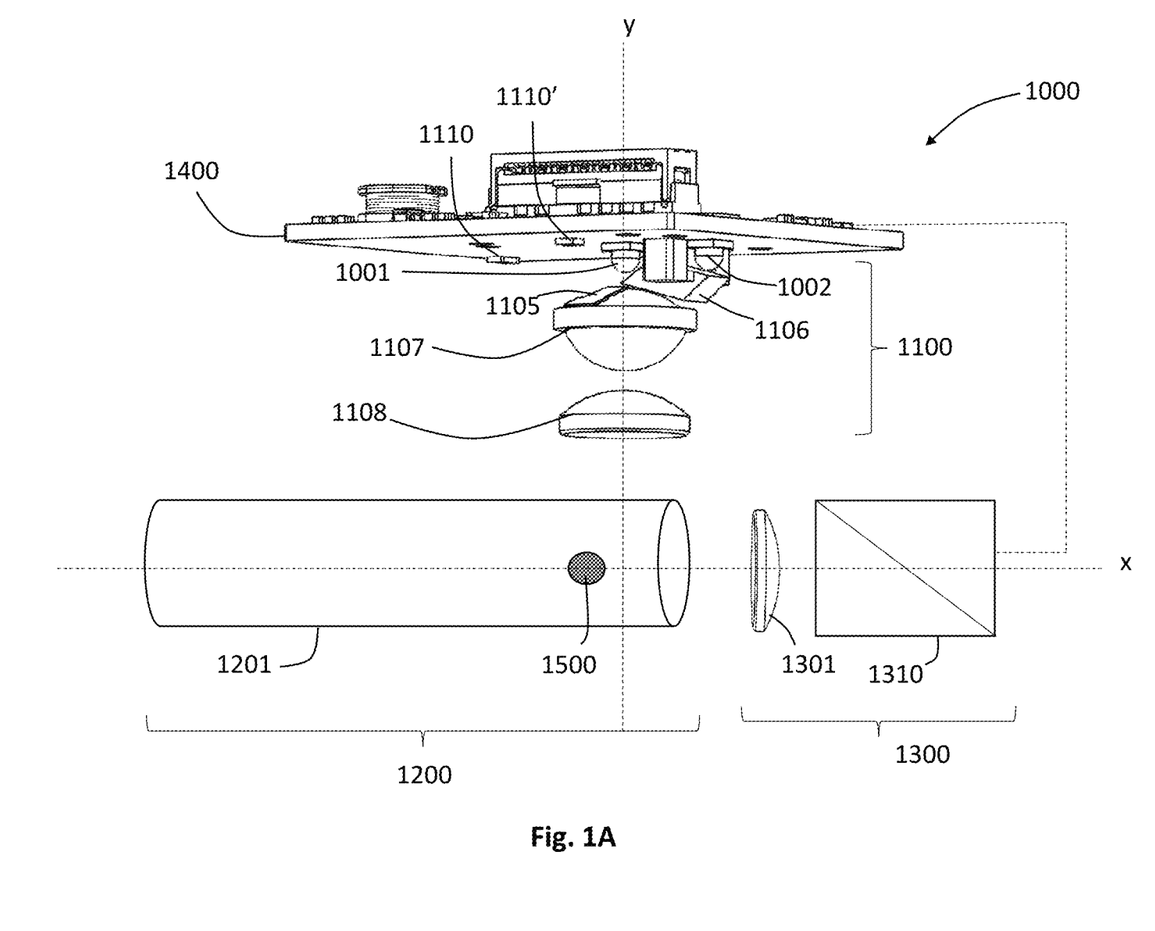
Figure 1B:
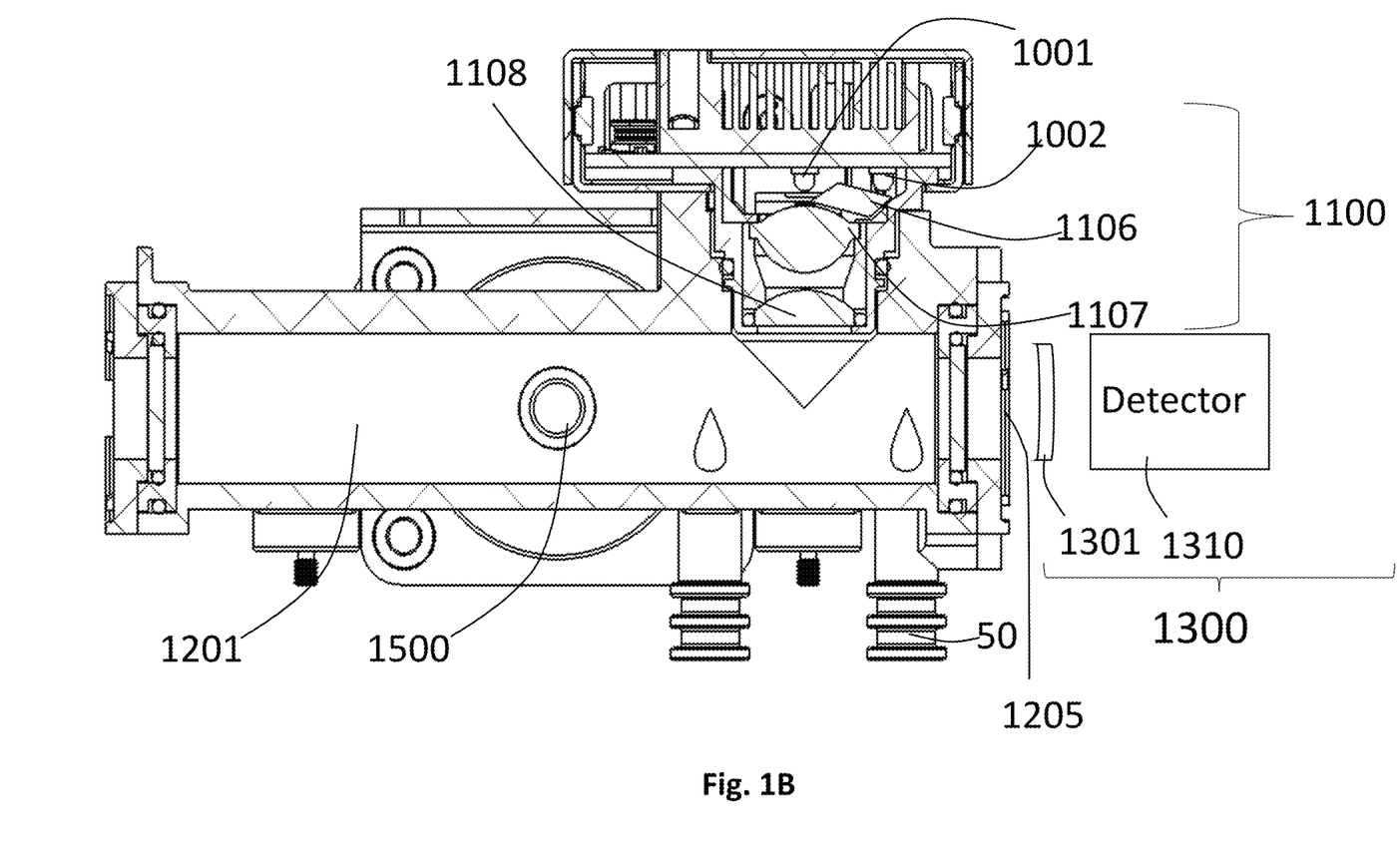

Reference is now made to FIG. 1A and FIG. 1B, schematically illustrating a system 1000 for monitoring a water sample from a water facility such as a swimming pool, according to some embodiments.

The system 1000 may include:
- a sampling unit 1200 including a cuvette 1201, which may be a fully or partially transparent container for containing therein a liquid sample such as a water sample, sampled from the water facility, where the cuvette 1201 may be of a cylindrical shape having a radial or any other symmetry about an axis "x" (as shown in FIG. 1A), which may be the optical axis of the spectral detector;
- a first (e.g. main) light source 1001 such as a LED lamp, e.g. emitting within a narrow WL band peaking at 420 nm;
- an additional light source 1002 used mainly for inspection of the first light source and/or analysis model, e.g. a LED lamp, emitting at a different narrow WL band peaking at 365 nm;
- an optical sensor 1110 such as an RGB sensor;
- an optical setup 1100 including a first (light) directing element 1105 such as a deflective/reflective element (e.g., mirror) and a second (light) directing element 1106 such as a pick-up prism or a beam splitter, and a collimating setup including a collimator 1107 and a focusing lens 1108.

The design, and functioning of each optical element of the optical setup 1100 and the relative positioning of the elements in respect to one another, are all configured for enabling directing a portion of the light source 1001/1002 that is operated, towards the optical sensor 1110 and another portion of light of the light source 1001/1002 towards the cuvette 1201 for irradiating the water sample therein;
- a detection unit 1300 including a spectral detector 1310, such as a spectrometer and a collimator or a focusing lens such as focusing lens 1301; and
- a processing unit 1400, such as a printed circuit board (PCB) as illustrated in FIG. 1A, operatively connected with the optical sensor 1110, the spectral detector 1310, and optionally also with the light sources 1001 and 1002.

As shown in FIGS. 1A and 1B, the collimator 1107, which may be a TIR (total-internal reflective) collimator or a PMMA (polymethyl methacrylate) collimator, may be optically aligned with the focusing lens 1108 (e.g., a plano-convex (PCX) lens), forming an axis "y", which may be perpendicular to the "x" axis.

According to some embodiments, the detection unit 1300 may be optically aligned along the "x" axis, that may be angular to (e.g., perpendicular to) axis "y", and located at a side of the cuvette 1201, for focusing the light exiting from the cuvette 1201 e.g., via a transparent exit wall 1205 (e.g. exit widow) of the cuvette 1201, by using the focusing lens 1301 and detecting (spectral) optical characteristics of the exiting light using the spectrometer 1310. The large angle of scattered light and the induced fluorescence light irradiated by the water sample may be coupled by the focusing lens 1301 located adjacent to a side of the cuvette 1201 of the sampling unit 1200, onto to the spectral detector 1310 input surface, which may be perpendicular to the axis "x", which may be the optical axis of the spectral detector 1310.

According to some embodiments, the system 1000 may be using one or more additional optical sensors such as sensor 1110'.

The processing unit 1400 may be configured, inter alia, to perform one or more of:
- control the operation of the optical sensor 1110, the spectral detector 1310 and/or of the light sources 1001/1002 (e.g. by switching them on/off for controlling which of the light sources is to be operated based on system requirements);
- receive and process/analyze updated data from the optical sensor 1110 and from the spectral detector 1310 for:
  (i) detecting turbidity level and/or biological and/or chemical pollutants quantity and/or concentration in the water sample (e.g., based on received updated spectral detector data and updated sensor data); and/or
  (ii) detecting other impairments in light source 1001 functionality, in analysis model, and/or in spectral detector 1310 functionality (e.g., based on spectral data only for the two separate light sources 1001 and 1002 acquired in a non-simultaneous manner, requiring switching to a different light source for each update detector data acquisition); and
- adjusting the analysis model, used for detection of optical characteristics of the water sample such as the turbidity level and/or pollutants' quantity/concentration, based on identified impairments.

According to some embodiments, the cuvette 1201, being a liquid container used for optical purposes, may be completely transparent in all its sides and walls or be partially-transparent having most of its structure walls non-transparent and parts thereof transparent, e.g. by having two or more transparent windows in at least two sides thereof: one first side window facing the optical setup 1100 and another second side window facing the detection unit 1300 (to enable light passed through the water sample to be detected by the spectral detector).

The light from the light source 1001 that is directed by the one or more directing elements of the optical setup 1100 towards the water sample in the sampling unit 1200, may be collimated and/or focused onto an area (spot) in the sample to maximizing the fluorescence signal coupled to the spectral detector 1310.

According to some embodiments, the water sample (herein also "sampled water") may continuously flow in the cuvette 1201 for measuring water-quality related characteristics of the actual water that is in the water facility (e.g., swimming pool) to avoid the sample from developing additional water-quality reducing problems such as inducing biomass growth. To enable continuous flow or frequent replacement of the water sample in the cuvette 1201, the cuvette 1201 may include one or more inlets and outlets (such as inlet/outlet 50), to enable, for example, water from the water facility to flow therethrough, based on water/air pressure differences (gradient) between different areas of the cuvette 1201 or a container/piping containing the cuvette 1201 therein. In some embodiments, an elaborated piping and pressure control system may be used, also optionally, as part of a more inclusive water flow and pressure control system of the water facility.

According to some embodiments, as shown in FIGS. 1A and 1B, the system 1000 may further include one or more acoustic devices such as an ultrasonic (US) acoustic transducer 1500, attached to the cuvette 1201, whereas the processing unit 1400 may be further configured to control, receive and process data/signals of the acoustic transducer 1500.

According to some embodiments, as mentioned above, the acoustic transducer(s) may be used for measuring water hardness rate of the water in the water facility and/or for cleaning the water sample and/or the cuvette.

Figure 2:
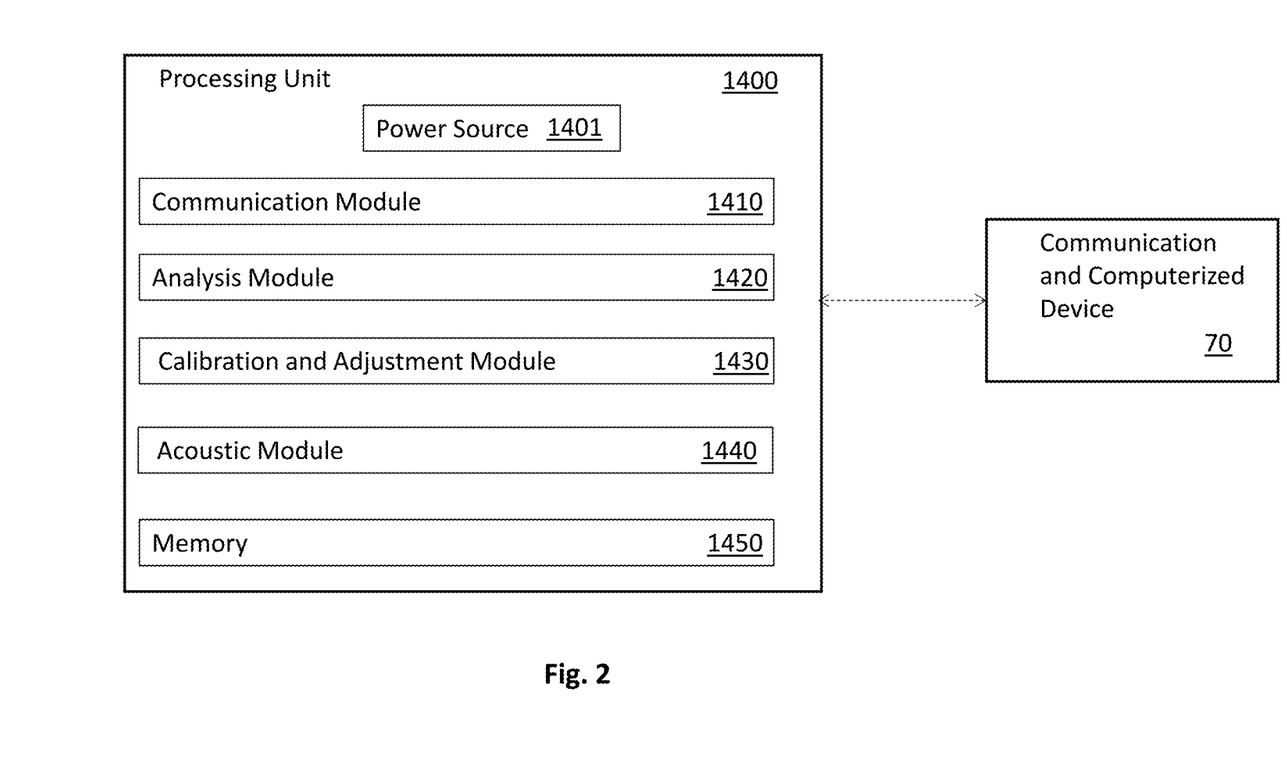
FIG. 2 shows a block diagram schematically illustrating modules of a processing unit of the system, according to some embodiments.

Reference is now made to FIG. 2 showing some optional modules operable by the processing unit 1400, according to some embodiments. The processing unit 1400 may include at least some of the following modules:

- a communication module 1410, configured to receive and/or transmit data and/or electrical signals from and/or to one or more of: the optical sensor 1110, the optical detector 1310, the acoustic transducer(s) 1500, the first (main) light source 1001 or a switching circuit thereof, the additional light source 1002 or a switching circuit thereof;
- an analysis module 1420, configured to receive updated data indicative of measured optical characteristics (spectrum and/or overall power/intensity etc.) emanating from the output data/signals of the spectral detector and optical sensor and analyze the received updated data to determine/detect one or more of: turbidity level of the sampled water; concentration/quantity of pollutants in the sampled water such as algae concentration (based on fluorescence and scattering detection); water-hardness rate; and/or system impairments;
- a calibration and adjustment module 1430 being configured for calibration and adjustment at least of an analysis model, used for determining of water characteristics including at least: turbidity level and/or pollutants concentration/quantity, where the adjustment/calibration is based on identified impairments of the system requiring analysis model adjustments (e.g., based on one or more model-adjustment rules, programs and/or criteria);
- an acoustic module 1440 configured for controlling the above-described process for measuring water-hardness rate; and
- a memory unit 1450 for retrievably and adjustably (changeably) storing thereby information required for performing all system 1000 operations such as for retrievably storing: programs and/or algorithms used for data analysis, received updated data, etc.

The processing unit may further include one or more continuous and/or chargeable power supply sources such as power source 1401.

Figure 3:
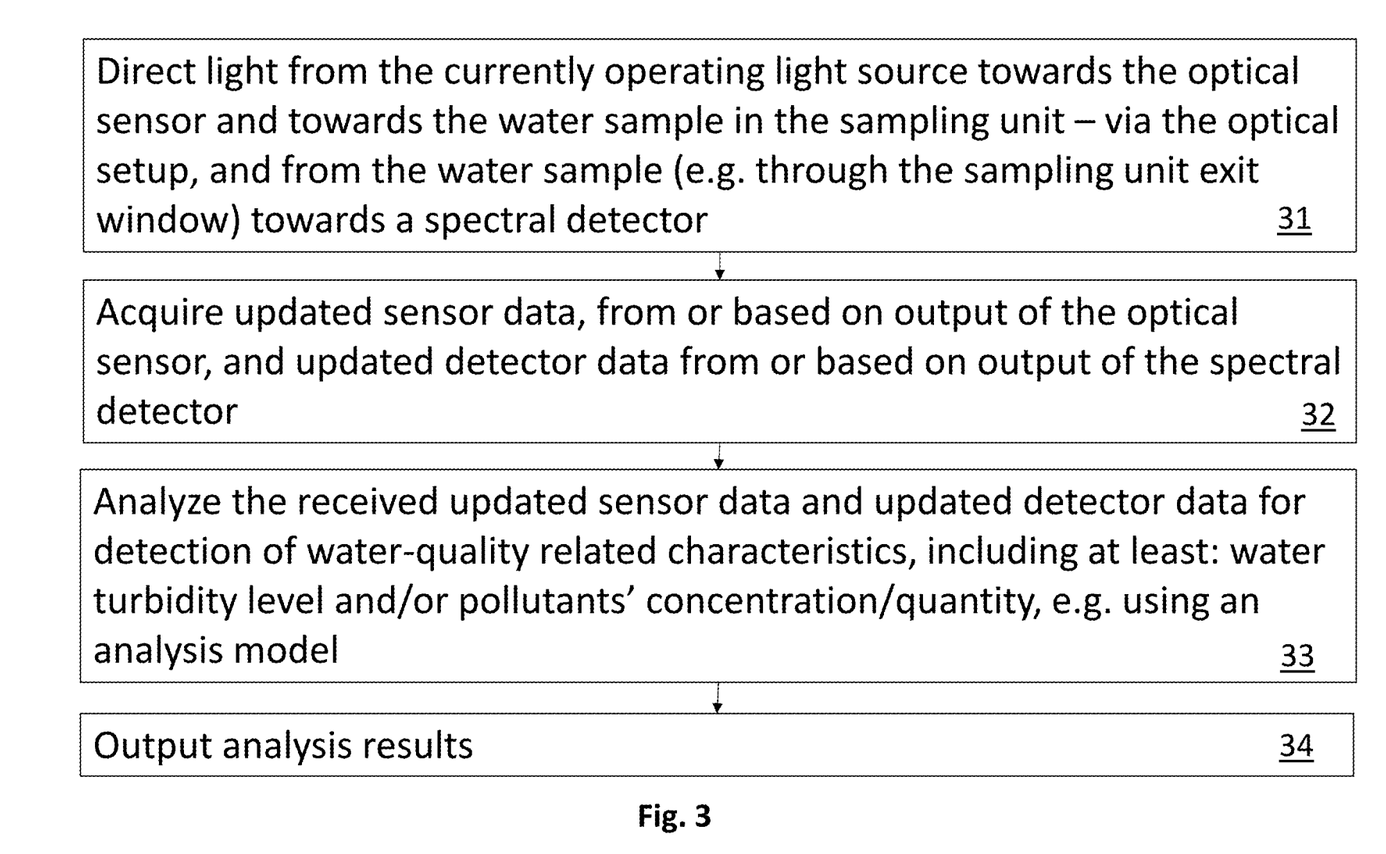
FIG. 3 shows a flowchart, schematically illustrating a process or method for measuring water-quality related characteristics of water sampled from a water facility, according to some embodiments.

According to some embodiments, the processing unit 1400 may be further configured to communicate with at least one communication and computerized device (CCD) 70 such as a main control system (using one or more computers and devices for controlling the system), a personal computer (PC), a mobile phone, a laptop device, a tablet device etc., e.g. for enabling at least one user to be updated with information relating to system operation, water-quality state etc. and optionally also to be able to control the system via the CCD 70, e.g. by using a designated user interface or input device Reference is now made to FIG. 3, which shows a flowchart illustrating a process of monitoring water-quality related characteristic using any one of the aforementioned monitoring system configurations. The monitoring process may include:

- directing light from the currently operating (selected) light source (the first (main light source e.g., of 420 nm or additional light source e.g., of 365 nm)—towards the optical sensor (for measuring overall intensity/power/amplitude of the currently operating light source) and towards the sampling unit (step 31), e.g. by using one or more optical elements of the optical setup;
- acquiring updated sensor data (which may be taken directly or deduced/calculated from the optical sensor output signal) and updated detector data (which may be taken directly or deduced/calculated from the spectral detector output signal) (step 32), where the updated sensor data may be indicative of the overall intensity/power of the operating light source, and the updated detector data may be indicative of spectral characteristics of light outputted from the sampling unit;
- analyzing the received updated sensor data and updated detector data (step 33) for detection of water-quality related characteristics including at least one of: water turbidity level, pollutant(s) quantity/concentration, an/or water-hardness rate, e.g. by using an analysis model; and
- outputting analysis results (step 34), e.g., by display, storage and/or transmission thereof.

Aspects of disclosed embodiments, pertain to systems and methods for monitoring water characteristics in a water facility, by selecting a light source from a first light source emitting light at a first WL peak, and an additional light source, emitting light at an additional WL peak which is distinctively different from the first WL peak; for each light source performing a measurement of a water sample taken from the water facility, using an optical sensor outputting updated sensor data and a spectral detector, outputting updated detector data; and determining adjustment properties for adjustment of an analysis model, based on comparison between the measurements for each of the light sources, the analysis model being used for on going determining of one or more water characteristics of the water sample including, for example, water turbidity level and/or chemical and/or biological pollutants' concentration/quantity/growth-rate, e.g. based on fluorescence and/or scattering characteristics of light exiting from the sampling unit.

Reference is now made to FIG. 4A, schematically illustrating a process for adjusting an analysis model, the analysis model used for determining water characteristics, according to some embodiments. The adjustment process may include:

- selecting a light source for operation from a first light source emitting light at a first wavelength (WL) peak, and at least one additional light source, emitting light at an additional WL peak which is distinctively different from the first WL peak (step 401);
- for each light source perform a measurement process of (step 402):
  (i) directing one portion of light, emanating from the selected light source, towards a sampling unit, holding therein a water sample of water from the water facility, and another portion of the light towards at least one optical sensor, wherein the directing is done using an optical setup comprising one or more optical elements;
  (ii) acquiring updated sensor data from the at least one optical sensor;
  (iii) acquiring updated detector data from a spectral detector, the spectral detector being configured and positioned to detect light irradiated by the sampling unit;
- receiving the acquired updated sensor data and the updated detector data for each of the light source's measurements (step 403); and
- determining adjustment properties for adjustment of an analysis model, based on comparison between the measurements for each of the light sources (step 4042).

Figure 4B:
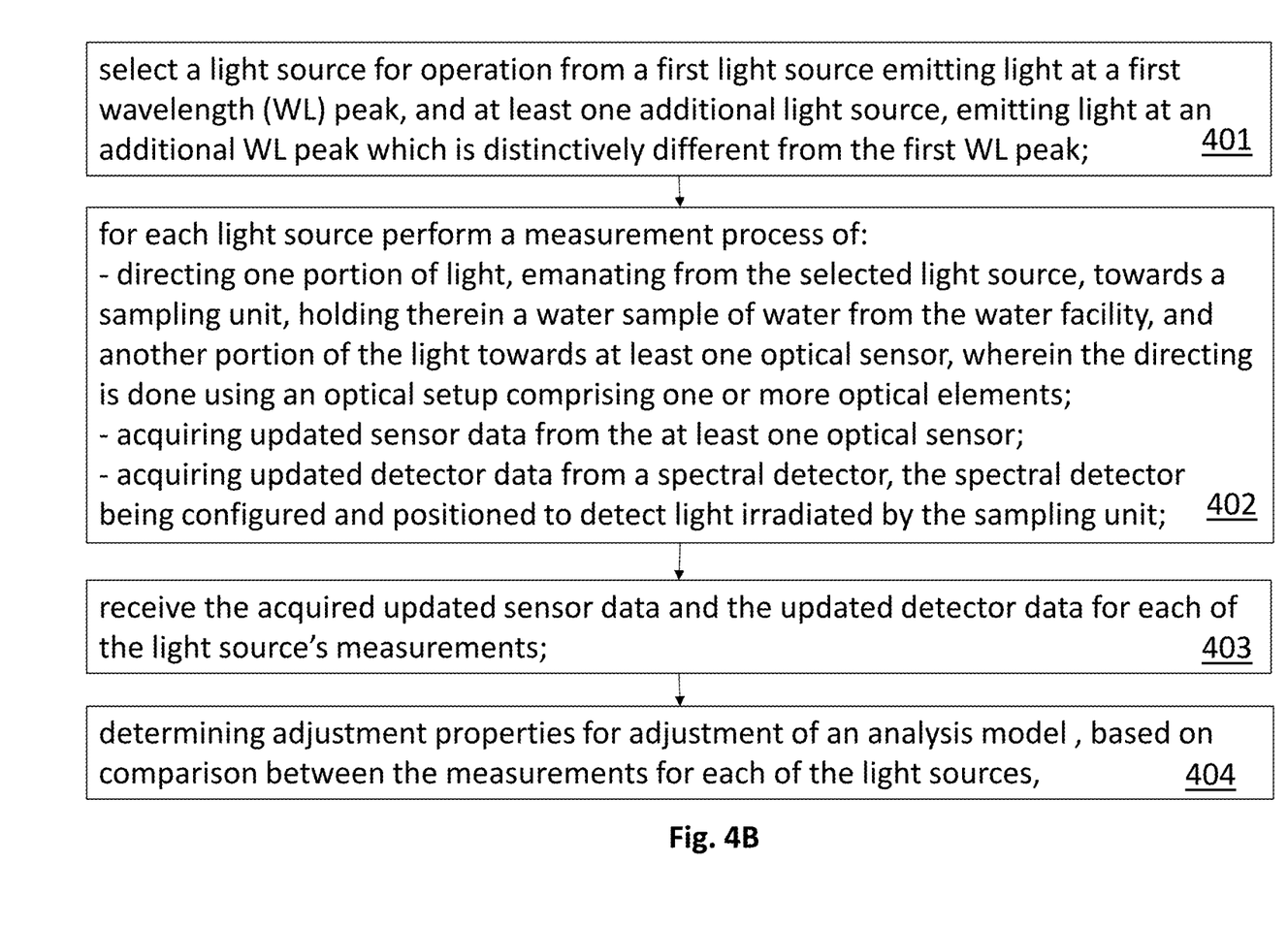
FIG. 4B shows a flowchart, schematically illustrating a process or method for identification of system impairments and calibration/adjustment of analysis model used for detection of the water-quality related characteristics, where the analysis model calibration/adjustment is based on identified system impairments, according to some embodiments.

Reference is now made to FIG. 4B, illustrating an inspection process for identification of system impairments (e.g., based on spectral analysis) and analysis model adjustment, based on identified impairments, according to some embodiments. The inspection process may require using "an inspection model", which may include any one or more software programs and/or hardware [processing means configured to receive and analyze data/signals for carrying out the system impairments inspection.

According to some embodiments, the inspection process may include:

- receiving/measuring updated detector data emanating from spectral measurements made by the spectral detector, when the operating light source in the system is the first (main) light source (e.g., the 420 nm LED) (step 41), this updated detector data associated with the first light source can be referred to shortly as the "updated main spectral data";
- switching to the additional light source (e.g., the 365 nm LED) (step 42);
- acquiring updated detector data for the additional light source (step 43)—referred to herein as the "updated reference spectral data";
- receiving and analyzing the updated and main spectral data using the inspection model (step 44) to identify/detect impairments in the system functioning and estimating causes of those impairments, for example, spectral drift impairments, that may be caused due to main light source impairments and/or due to spectral detector impairments;
- the inspection model may further be programmed or designed to perform a decision-making process, for determining whether one or more of the identified impairment require adjustment/calibration of the analysis model, used for the water-quality monitoring, or not (step 45), e.g. based on one or more rules and/or criteria, and adjust the analysis model (step 46) if adjustment is determined as required; and
- if no adjustment is required, the processing unit may switch the light sources back again, for having the main first light source operated (step 471) and revert the system operation back to performing its ongoing water-quality monitoring mode, until another (next) inspection is required (step 48).

According to some embodiments, the entire inspection process may be initiated and operated automatically on a prescheduled frequent basis, upon identification of a drastic change in spectral measurements made for water-quality monitoring purposes, and/or upon receiving an inspection requirement from a user.

According to some embodiments, as mentioned above, the criteria for deciding that analysis model adjustment is required may include one or more of:

- a spectral drift exceeding a drift threshold or range; and/or
- a spectral drift caused due to spectral detector impairments;

According to some embodiments, other impairments and/or causes thereof may require a different active response such as complete shut down of the monitoring system and transmission of alert messages to one or more users, e.g., in cases in which one of the system components such as one of the detectors/sensors or main light source is malfunctioning.

Figure 5:
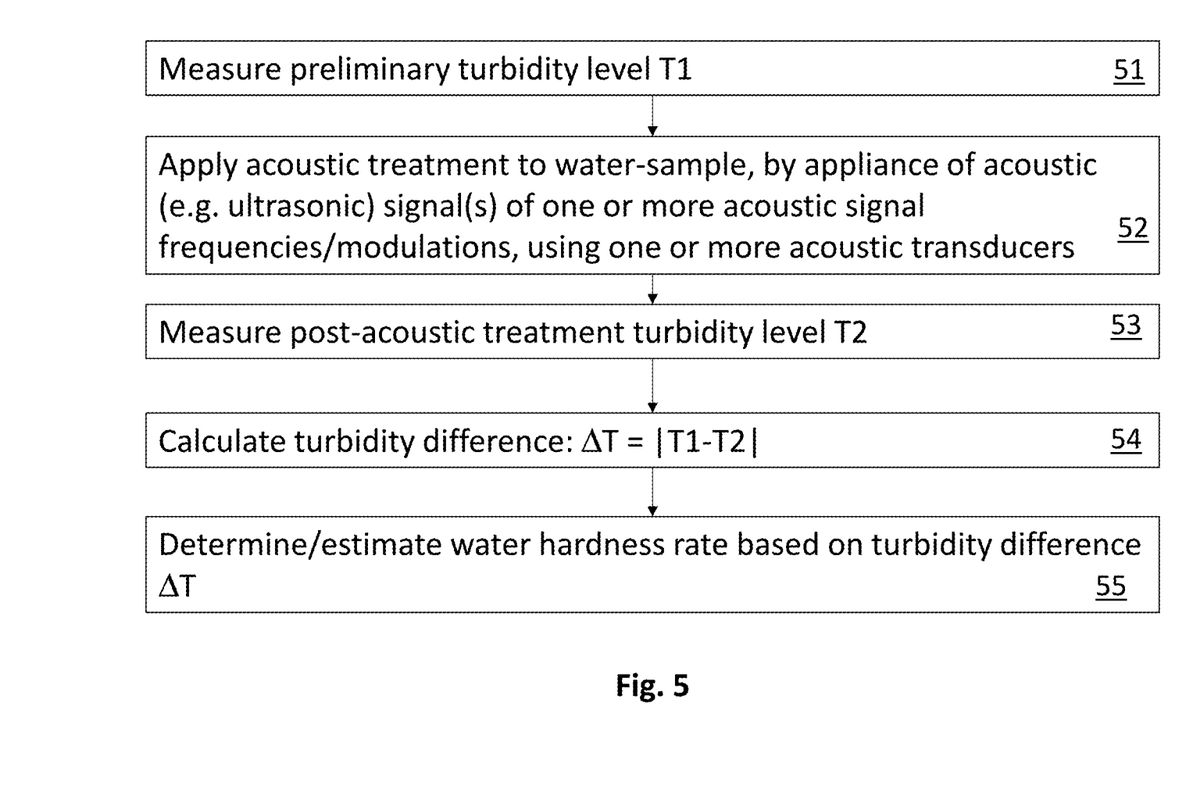
FIG. 5 shows a flowchart illustrating a water hardness rate testing process, based on acoustic signal transducing, according to some embodiments.

Reference is now made to FIG. 5, schematically illustrating a process of water-hardness rate detection, according to some embodiments. The water-hardness detection process may include:

- measuring a preliminary (pre-treatment) turbidity level $T_1$ of the sampled water right before applying an acoustic treatment (step 51);
- applying an acoustic treatment to the water sample for a predefined time period dt (step 52) (e.g., by using one or more ultrasonic acoustic transducers outputting acoustic signals in one or more frequencies/, modulations);
- measuring the turbidity level $T_2$ right or shortly after the acoustic treatment is ended (step 53);
- calculating the difference in turbidity measurements before and after the acoustic treatment (step 54): $DT=|T_2-T_1|$; and
- determining, based on the calculated turbidity difference DT, water-hardness level of the water in the water facility (step 55).

EXAMPLES

Example 1 is a system for automatic and ongoing monitoring of water in a water facility, the system comprising: a sampling unit comprising a water sample, sampled from the water facility;

a first light source configured to emit light of a distinctive first wavelength (WL) peak;

at least one additional light source configured to emit light of a distinctive second WL peak, which is distinctively different from the first WL peak;

an optical sensor configured to detect at least intensity related characteristic of light and output updated sensor data indicative of the at least intensity characteristic of light sensed thereby;

an optical setup, comprising at least one optical element, the optical setup being configured to direct light emitted by the first light source towards the optical sensor and towards the sampling unit such that the light emitted by the first light source irradiates the water sample in the sampling unit for enabling scattering and/or fluorescence of the light by the water sample;

at least one spectral detector, configured and positioned such as to detect spectral characteristics of light exiting from the sampling unit and output updated detector data indicative of the spectral characteristics of light detected thereby; and a processing unit configured to receive updated sensor data from the at least one optical sensor and updated detector data from the at least one spectral detector, perform an analysis of the received updated detector and sensor data, using an analysis model, and determine, based on the data analysis, one or more updated characteristics of the sampled water, the one or more updated characteristics comprising at least an updated turbidity level of the sampled water, wherein the processing unit is further configured to control operation of each of the first and additional light sources for analysis model adjustment purposes, wherein the analysis model adjustment is carried out by using updated sensor and detector data from at least two measurements, each measurement operating a different light source.

In example 2, the subject matter of example 1 may include, wherein the adjustment of the analysis model is carried out by determining values of one or more factors, thresholds or parameters of the analysis model, the analysis model adjustment being based on comparison between the at least two measurements, each using a different light source.

In example 3, the subject matter of examples 1 to 2 may include, wherein each of the first light source and the additional light source emits light in the ultraviolet range between 300-450 nm wherein the first light source emits light of a WL that is distinctly different than the emission WL of the additional light source.

In example 4, the subject matter of examples 1 to 3 may include, wherein the processing unit is further configured to adjust the analysis model, based on determined performances and/or impairments of the spectral detector or of the first light source.

In example 5, the subject matter of examples 1 to 4 may include, wherein the optical setup comprises: a first light directing element; a second light directing element; a collimator; and a focusing lens, wherein:

the first light directing element is configured and positioned to direct light emanating from any one of: the first light source and the at least one additional light source, whichever is operated, towards the collimator, the second light directing element is configured and positioned to direct light emanating from any one of: the first light source and the at least one additional light source, and/or from the first directing element, towards the at least one optical sensor, the collimator is configured and positioned to collimated directed thereto and further direct the light towards the focusing lens, and the focusing lens is positioned and configured to focus light directed thereto, onto the water sample in the sampling unit.

In example 6, the subject matter of examples 1 to 5 may include, wherein the sampling unit comprises a cuvette, for holding therein the water sample, the cuvette being at least partially transparent such as to enable receiving light directed thereto by the optical setup and exit of light therefrom towards the spectral detector.

In example 7, the subject matter of example 6 may include, wherein the system further comprises at least one acoustic transducer configured and positioned such as to acquire acoustic data of the water sample for determining an updated water hardness level of the sampled water, for determining cleanliness state of the cuvette and/or for cleaning the cuvette.

In example 8, the subject matter of example 7 may include, wherein the at least one acoustic transducer is configured to transmit and/or receive acoustics signals within the ultrasonic (US) frequency range.

In example 9, the subject matter of example 8 may include, wherein the US frequency range is between 10-40 kHz.

In example 10, the subject matter of examples 7 to 9 may include, wherein the determining of the updated hardness state of the water sample, the following process is performed, using the at least one acoustic transducer:

measuring a pre-US-treatment turbidity level $T_1$ of the water sample;

applying an ultrasonic treatment to the water sample by applying of US signals to the water sample;

measuring updated post-US-treatment turbidity level $T_2$ of the water sample, after the applying of the US treatment;

comparing the pre-US-treatment turbidity level $T_1$ with the post-US-treatment turbidity level $T_2$; and determining an updated water-hardness rate of the water sample, based on the comparison results.

In example 11, the subject matter of examples 1 to 10 may include, wherein the one or more updated characteristics of the sampled water determined by the processing unit further comprises one or more of: concentration, type, growth rate and/or quantity of biomass; concentration, type and/or quantity of chemical pollutants; Ph level; water temperature; water hardness rate; cuvette cleanliness state.

In example 12, the subject matter of examples 1 to 11 may include, wherein the system further comprises one or more additional sensors for sensing additional characteristics of the water sample and/or of the system.

In example 13, the subject matter of example 12 may include, wherein the one or more additional sensors comprise a thermal sensor positioned and configured to sense temperature in an area of the first light source.

In example 14, the subject matter of examples 1 to 13 may include, wherein the processing unit comprises one or more of:

a communication module, configured to receive and/or transmit data and/or electrical signals from and/or to one or more of: the at least one optical sensor, the spectral detector, the acoustic transducer, the first light source or a switching circuit thereof, an additional light source or a switching circuit thereof;

an analysis module, configured to receive updated data at least from the at least one sensor and from the spectral detector and analyze the received updated data to determine one or more of characteristics of the water and/or of the system, using an analysis model;

a calibration and adjustment module being configured for calibration and adjustment at least of the analysis model, based on determined characteristics of the system, by controlling operation of each of the light sources;

a memory unit for retrievable storage of information required for performing all system operations and updated data; and one or more continuous and/or chargeable power supply sources.

In example 15, the subject matter of example 14 may include, wherein the analysis model is configured to determine turbidity level of the sampled water and/or concentration/quantity of pollutants in the sampled water, based on relation between the overall intensity or power of the light source, indicated in the updated sensor data, and the overall intensity or power of light detected by the spectral detector, associated with fluorescence and/or scattered light exiting from the sampling unit.

In example 16, the subject matter of examples 1 to 15 may include. Wherein the system further comprises a detection unit comprising the spectral detector and at least one optical element positioned and configured to collimate or focus light onto an input surface of the spectral detector.

In example 17, the subject matter of examples 1 to 16 may include, wherein an angle between an optical axis "x" that is perpendicular to the input surface of the spectral detector, and a "y" axis defined by at least part of the directionality of the light directed from the light source to the sampling unit ranges between 10-90 degrees.

In example 18, the subject matter of examples 1 to 17 may include, wherein the optical detector comprises a spectrometer.

In example 19, the subject matter of examples 1 to 18 may include, wherein the optical sensor comprises one or more of: a photodiode, a photodetector, a RGB sensor, a charged coupled device (CCD).

Example 20 is a method for automatic and ongoing monitoring of water in a water facility, the method comprising:

selecting a light source for operation from a first light source emitting light at a first wavelength (WL) peak, and at least one additional light source, emitting light at an additional WL peak which is distinctively different from the first WL peak;

for each light source perform a measurement process of:
directing one portion of light, emanating from the selected light source, towards a sampling unit, holding therein a water sample of water from the water facility, and another portion of the light towards at least one optical sensor, wherein the directing is done using an optical setup comprising one or more optical elements;
acquiring updated sensor data from the at least one optical sensor;
acquiring updated detector data from a spectral detector, the spectral detector being configured and positioned to detect light irradiated by the sampling unit;
receiving the acquired updated sensor data and the updated detector data for each of the light source's measurements; and
determining adjustment properties for adjustment of an analysis model, based on comparison between the measurements for each of the light sources,
wherein the analysis model is used for ongoing analysis of received updated sensor and detector data for determining one or more water characteristics of the water sample.

In example 21, the subject matter of example 20 may include, wherein the adjustment of the analysis model is carried out by determining values of one or more factors, thresholds or parameters of the analysis model.

In example 22, the subject matter of examples 20 to 21 may include, wherein each of the first light source and the additional light source emits light in the ultraviolet range of between 300-450 nm and wherein the first light source emits light at a distinctly different WL than that of the additional light source.

In example 23, the subject matter of examples 20 to 22 may include, wherein the method further comprises: determining performances and/or impairments of the spectral detector or of the first light source, wherein the adjustment of the analysis model is also based on determined performances and/or impairments.

In example 24, the subject matter of examples 20 to 23 may include, wherein the method further comprises: acquiring acoustic data of the water sample, using at least one acoustic transducer, and determining an updated water hardness level of the sampled water, for determining cleanliness state of the cuvette and/or for cleaning the cuvette.

In example 25, the subject matter of example 24 may include, wherein the at least one acoustic transducer is configured to transmit and/or receive acoustics signals within the ultrasonic (US) frequency range.

In example 26, the subject matter of example 25 may include, wherein the US frequency range is between 10-40 kHz.

In example 27, the subject matter of examples 24 to 26 may include, wherein the determining of the updated hardness state of the water sample, the following process is performed, using the at least one acoustic transducer:

measuring a pre-US-treatment turbidity level $T_1$ of the water sample;
applying an ultrasonic treatment to the water sample by applying of US signals to the water sample;
measuring updated post-US-treatment turbidity level $T_2$ of the water sample, after the applying of the US treatment;
comparing the pre-US-treatment turbidity level $T_1$ with the post-US-treatment turbidity level $T_2$; and
determining an updated water-hardness rate of the water sample, based on the comparison results.

In example 28, the subject matter of examples 20 to 27 may include, wherein the one or more updated characteristics of the sampled water abled to be determined by the analysis model comprises one or more of: turbidity level; concentration, type, growth rate and/or quantity of biomass; concentration, type and/or quantity of chemical pollutants; Ph level; water temperature; water hardness rate; and/or cuvette cleanliness state.

In example 29, the subject matter of examples 20 to 28 may include, wherein the method further comprises: sensing temperature in an area of the light sources, using at least one thermal sensor.

In example 30, the subject matter of examples 20 to 29 may include, wherein the analysis model is configured to determine turbidity level of the sampled water and/or concentration/quantity of pollutants in the sampled water, based on relation between the overall intensity or power of the light source, indicated in the updated sensor data, and the overall intensity or power of light detected by the spectral detector, associated with fluorescence and/or scattered light exiting from the sampling unit.

In example 31, the subject matter of examples 20 to 30 may include, wherein the optical detector comprises a spectrometer.

In example 32, the subject matter of examples 20 to 31 may include, wherein the optical sensor comprises one or more of: a photodiode, a photodetector, a RGB sensor, a charged coupled device (CCD).

Example 33 is a method for automatic and ongoing monitoring of water in a water facility, the method comprising:
selecting a light source from a first light source emitting light at a first wavelength (WL) peak, and at least one additional light source, emitting light at an additional WL peak which is distinctively different from the first WL peak;
for each light source, performing a measurement of a water sample taken from the water facility, using an optical sensor outputting updated sensor data and a spectral detector, outputting updated detector data; and
determining adjustment properties for adjustment of an analysis model, based on comparison between the measurements for each of the light sources, the analysis model being used for ongoing determining of one or more water characteristics of the water sample.

In example 34, the subject matter of examples 33 may include, wherein the one or more water characteristics of the water sample including one or more of: water turbidity level; water chemical and/or biological pollutants' concentration, quantity and/or growth-rate.

In example 35, the subject matter of example 34 may include, wherein the determination of the turbidity level and/or concentration/quantity of pollutants in the sampled water is based on relation between the overall intensity or power of the light source, indicated in the updated sensor data, and the overall intensity or power of light detected by the spectral detector, associated with fluorescence and/or scattered light exiting from the sampling unit.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments and/or by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Any electronic and/or digital computerized system, unit, processing module, device and/or engine disclosed in an exemplary manner herein, may be programmable to perform particular functions pursuant to computer readable and executable instructions, rules, conditions, criteria, etc. from programmable hardware and/or software based execution modules/units/models/algorithms that implement one or more methods or processes disclosed herein, can in effect be considered as pertaining to a "designated purpose computer", "special purpose computer", "special purpose processing device" etc.

The models, methods and/or processes disclosed herein may be implemented as a computer program/algorithm that may be embodied in a non-transitory tangible computer-readable and/or non-transitory tangible machine-readable storage device or devices. The computer program product may directly loadable into an internal memory of a digital computer, comprising software code portions for performing the methods and/or processes as disclosed herein.

The terms "computer-readable storage device/machine" and "non-transitory machine-readable storage device" encompasses intermediate or stationary storage media, execution memory of a computer, and any other medium or device capable of retrievable storage of information. A computer program, algorithm, instructions or model can be deployed to be executed on one or more computer devices or distributed across multiple other computers via one or more communication networks.

These computer readable and executable instructions may be provided to a processor of a general purpose computer, special purpose computer, or other programmable data processing apparatus to produce a machine, such that the instructions/commands, which are executed via the processor of the computer or other programmable data processing apparatus enable implementation of the functions/acts specified in aforementioned flowcharts and/or block diagrams etc.

A system, a module, a device, a mechanism, a unit and or a subsystem may each comprise a machine or machines executable instructions (e.g. commands) and optionally also data storage, communication, processing and outputting means. A module, a program or a model may be implementable by a digital and/or electrical circuit, such as a printed circuit for causing the system to implement the method, process and/or operation as disclosed herein.

Unless otherwise specified, the terms "substantially", "about", "approximately" and the like, may be considered to be within an inclusive range of −10% to +10% of the respective magnitude or value.

Terms used in the singular shall also include the plural, except where expressly otherwise stated or where the context otherwise requires.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

The number of elements shown in the Figures should by no means be construed as limiting and is for illustrative purposes only.

Each system, device, unit, apparatus, method or process described above by way of using an image such as: a flowchart, an illustrating drawing and/or diagrams is not limited to the particular image being used, whereby the illustrated object such as process, device or system, may include more or less components or steps than those indicated in the particular image.

The invention claimed is:

1. A system configured for monitoring water from a water facility, the system comprising:
    a sampling unit comprising a water sample, sampled from the water facility;
    at least two light sources, each configured to emit light of a different wavelength (WL) peak, for illuminating the water sample in the sampling unit;
    at least one spectral detector, configured and positioned to detect spectral characteristics of light exiting from the sampling unit, when illuminated by each of the at least two light sources, and output updated detector data indicative of updated spectral characteristics of light detected thereby; and
    a processing unit configured to receive and analyze:
    (i) updated detector data from the at least one spectral detector associated at least with updated spectral measurement of the water sample obtained when the water sample therein was illuminated by the at least two light sources, and
    (ii) assumed WL peaks of each of the at least two light sources, and perform spectral analysis of the received updated detector data, using an analysis model, to determine, one or more updated characteristics of the sampled water,
    wherein the processing unit is further configured to determine spectral shifts between assumed WL peaks of the at least two light sources and measured WL peaks of the at least two light sources, measured by the at least one spectral detector, for adjusting spectral analysis of the updated detector data arriving from the at least one spectral detector, used for determination of one or more characteristics of the water sample, based on determined spectral shifts.

2. The system of claim 1, wherein the assumed WL peaks of the at least two light sources are obtained by one or more of:
    conducting one or more premeasurements of the WL peak of each of the at least two light sources under same and/or varying conditions;
    retrieving or receiving known values of assumed WL peaks of the at least two light sources; and/or
    conducting ongoing direct measurements of the WL peaks of the at least two light sources, using at least one optical sensor configured and positioned to directly measure the WL peaks of the at least two light sources.

3. The system of claim 1 further comprising an optical setup that is configured to direct light emitted by the one or more of the at least two light sources, towards the sampling unit.

4. The system of claim 1 further comprising:
    at least one optical sensor positioned and configured to detect at least intensities of light emitted by each of the at least two light sources; and
    an optical setup, comprising at least one optical element, the optical setup being configured to direct light emitted by the one or more of the at least two light sources, towards the at least one optical sensor and towards the sampling unit,
    wherein the processing unit is further configured to receive updated sensor data from the at least one optical sensor and to determine the spectral shifts of the WL peaks, by determining WL peak differences between WL peaks of the light sources, directly measured by the at least one optical sensor, and spectrum of the water sample measured by the at least one spectral detector.

5. The system of claim 3, wherein the optical setup comprises:
    a first light directing element;
    a second light directing element;
    a collimator; and
    a focusing lens,
    wherein:
    the first light directing element is configured and positioned to direct light emanating from any one or more of the at least two light sources, towards the collimator,
    the second light directing element is configured and positioned to direct light emanating from one or more of the at least two light sources, and/or from the first directing element, towards at least one optical sensor,
    the collimator is configured and positioned to collimate light directed thereto and further direct the light towards the focusing lens, and
    the focusing lens is positioned and configured to focus light directed thereto onto the water sample in the sampling unit.

6. The system of claim 1 further comprising at least one acoustic transducer configured and positioned such as to transmit and/or receive acoustic signals, acquire acoustic data of the water sample and/or apply acoustic signals over the water sample, for determining an updated water hardness level of the water sample, for determining a cleanliness state of a cuvette of the sampling unit and/or for cleaning the cuvette.

7. The system of claim 6, wherein the frequency of the acoustic signals transmitted by the at least one acoustic transducer ranges between 10-40 kHz and/or wherein the determining of the updated hardness state of the water sample, using the at least one acoustic transducer, is performed by one or more of:
    measuring a pre-acoustic-treatment turbidity level T1 of the water sample;
    acoustically treating the water sample by applying acoustic signals to the water sample;
    measuring updated post-acoustic-treatment turbidity level T2 of the water sample, after the applying of the acoustic treatment;
    comparing the pre-acoustic-treatment turbidity level T1 with the post-acoustic treatment turbidity level T2; and
    determining an updated water-hardness of the water sample, based on the comparison results.

8. The system of claim 1, wherein the one or more updated characteristics of the water sample determined by the processing unit further comprises one or more of:
- concentration, type, growth rate and/or quantity of biomass;
- concentration, type and/or quantity of chemical substances;
- water turbidity level;
- pH level;
- water temperature;
- water hardness; and
- cuvette cleanliness state.

9. The system of claim 1 further comprising one or more sensors for sensing additional characteristics of the water sample and/or of the system.

10. The system of claim 9, wherein the one or more sensors are configured for sensing at least one of: temperature of the water sample and/or the system, conductivity of the water sample, and water hardness of the water sample.

11. The system of claim 10, wherein the one or more sensors comprise a thermal sensor positioned and configured to sense temperature in an area of at least one of the at least two light sources.

12. The system of claim 1, wherein the processing unit comprises one or more of:
- a communication module, configured to receive and transmit data or electrical signals;
- an analysis module, configured to receive updated detector data and analyze the received updated data to determine one or more characteristics of the water sample and/or of the system;
- a calibration and adjustment module being configured for calibration and adjustment at least of the analysis of the updated detector data;
- an acoustic module configured for controlling one or more acoustic transducers, receive and analyze acoustic data;
- a memory unit configured for retrievable storage of information required for performing all system's monitoring, control, adjustment and/or calibration operations, updated devices data and/or data analysis results; and
- one or more continuous and/or chargeable power supply sources.

13. The system of claim 1, wherein an angle between an optical axis "x" that is perpendicular to an input surface of the at least one spectral detector, and a direction of light, emanating from one or more of the at least two light sources, that impinges the sampling unit, ranges between 10-90 degrees.

14. A method for monitoring water from a water facility, the method comprising:
- illuminating a water sample held in a sampling unit, using at least two light sources, configured to emit light in at least two different wavelength (WL) peaks;
- detecting updated WL peaks of the water sample using updated detector data from at least one spectral detector;
- receiving assumed WL peaks of the at least two light sources;
- determining spectral shifts between assumed WL peaks of each of the at least two light sources and detected updated WL peaks of the water sample, the assumed WL peak of each light source, being estimated or known; and
- adjusting spectral analysis of the updated detector data used for determination of one or more characteristics of the water sample, based on determined spectral shifts.

15. The method of claim 14, wherein the assumed WL peaks of the at least two light sources are obtained by one or more of:
- conducting one or more premeasurements of the WL peak of each of the at least two light sources under same and/or varying conditions;
- retrieving or receiving known values of assumed WL peaks of the at least two light sources; and/or
- conducting ongoing direct measurements of the WL peaks of the at least two light sources, using at least one optical sensor configured and positioned to directly measure the WL peaks of the at least two light sources.

16. The method of claim 15 further comprising receiving updated sensor data from at least one optical sensor positioned and configured to detect light emanating from the at least two-light sources for determining each light source currently illuminating the water sample, wherein the spectral shifts are further determined by determining WL peak differences between light sources' WL peaks directly measured by the at least one optical sensor and spectrum of the water sample measured by the at least one spectral detector.

17. The method of claim 16, wherein the at least one optical sensor comprises at least one red-green-blue (RGB) sensor or an additional spectral sensor.

18. The method of claim 14 further comprising one or more of:
- determining performances and/or impairments of the spectral detector or of the at least two light sources, based on determined spectral shifts;
- acquiring acoustic data of the water sample, using at least one acoustic transducer, configured to receive and transmit acoustic signals within the ultrasonic (US) acoustic range; and
- determining an updated water hardness of the water sample, for determining a cleanliness state of a cuvette and/or for cleaning the sampling unit sensing temperature in an area of the at least two light sources, using at least one thermal sensor.

19. The method of claim 18, wherein the determining an updated hardness state of the water sample, the following process is performed, using the at least one acoustic transducer:
- measuring a pre-acoustic-treatment turbidity level T1 of the water sample;
- applying an acoustic treatment to the water sample by applying of acoustic signals to the water sample;
- measuring updated post-acoustic-treatment turbidity level T2 of the water sample, after the applying of the acoustic treatment;
- comparing the pre-acoustic-treatment turbidity level T1 with the post-acoustic-treatment turbidity level T2; and
- determining an updated water-hardness of the water sample, based on the comparison results.

20. The method of claim 14, wherein the determination of spectral shifts of the spectral detector is done in a calibration stage under known conditions and/or as an ongoing process under unknown conditions.

* * * * *